(12) United States Patent
Kobayashi et al.

(10) Patent No.: US 6,677,984 B2
(45) Date of Patent: Jan. 13, 2004

(54) ELECTRONIC ENDOSCOPE SYSTEM

(75) Inventors: Hiroyuki Kobayashi, Tokyo (JP); Hideo Sugimoto, Tokyo (JP)

(73) Assignee: Pentax Corporation, Tokyo (JP)

( * ) Notice: Subject to any disclaimer, the term of this patent is extended or adjusted under 35 U.S.C. 154(b) by 506 days.

(21) Appl. No.: 09/725,200

(22) Filed: Nov. 29, 2000

(65) Prior Publication Data

US 2001/0002141 A1 May 31, 2001

(30) Foreign Application Priority Data

Nov. 30, 1999  (JP) ............................. P11-339580

(51) Int. Cl.$^7$ ............................. H04N 7/18; H04N 9/47; A62B 1/04
(52) U.S. Cl. ............................. 348/65; 348/45
(58) Field of Search ............................. 348/65, 67, 68, 348/71, 72, 45; 600/109, 111; H04N 7/18, 9/47; A62B 1/04

(56) References Cited

U.S. PATENT DOCUMENTS

| 4,615,330 | A | * | 10/1986 | Nagasaki et al. | ............ 600/104 |
| 4,933,757 | A | * | 6/1990 | Kanno et al. | ................. 348/71 |
| 5,049,989 | A | * | 9/1991 | Tsuji | ............................. 348/71 |
| 5,178,130 | A | * | 1/1993 | Kaiya | ........................... 600/109 |
| 5,408,265 | A | * | 4/1995 | Sasaki | ........................... 348/70 |
| 5,604,530 | A | * | 2/1997 | Saito et al. | .................... 348/70 |
| 6,154,248 | A | * | 11/2000 | Ozawa et al. | .................. 348/65 |
| 6,567,114 | B2 | * | 5/2003 | Takahashi et al. | ............. 348/71 |

* cited by examiner

*Primary Examiner*—Nhon Diep
(74) *Attorney, Agent, or Firm*—Greenblum & Bernstein, P.L.C.

(57) ABSTRACT

In an electronic endoscope system, a scope has a solid image sensor provided at a distal end thereof to generate image-pixel signals. An image-signal processing unit produces a video signal based on the image-pixel signals. An alteration system alters a peak-to-peak level of a synchronizing-signal component of the video signal. An manual setting system manually operates the alteration system to perform the alteration of the peak-to-peak level of the synchronizing-signal component.

9 Claims, 9 Drawing Sheets

ELECTRONIC ENDOSCOPE SYSTEM

BACKGROUND OF THE INVENTION

1. Field of the Invention

The present invention relates to an electronic endoscope system including a scope having a solid image sensor provided at a distal end thereof to generate image-pixel signals, an image-signal processing unit that produces a video signal on the basis of the image-pixel signals, and a TV monitor for reproducing and displaying an image in accordance with the video signal.

2. Description of the Related Art

In general, in such an electronic endoscope system, a component-type color video signal is produced on the basis of image-pixel signals obtained from a solid image sensor, such as a CCD (charge-coupled device) image sensor, to reproduce an image of high quality on a TV monitor. Usually, the component-type color video signal is composed of three-primary-color video signal components and a compound-synchronizing-signal component which includes various synchronizing signals, such as a horizontal synchronizing signal, a vertical synchronizing signal and so on.

As is well known, the compound-synchronizing-signal component is produced as a voltage signal, and the peak-to-peak level of the voltage signal is standardized to, for example, 4 volts. Thus, a medical TV monitor, used in the electronic endoscope system, is designed in accordance with the compound-synchronizing-signal component exhibiting the peak-to-peak level of 4 volts.

Since the medical TV monitor is expensive, a domestic TV monitor may be frequently substituted for the medical TV monitor. Nevertheless, domestic TV monitors are not designed so as to accept the compound-synchronizing-signal component exhibiting the peak-to-peak level of 4 volts. Thus, the domestic monitors cannot properly function and display an image even though being connected to the image-signal processing unit.

Especially, after an electronic endoscope system with a medical TV monitor is introduced into a medical facility, when the medical TV monitor is replaced by a domestic TV monitor, or when a domestic TV monitor is added to the introduced electronic endoscope system, a problem will occur.

SUMMARY OF THE INVENTION

Therefore, an object of the present invention is to provide an electronic endoscope system comprising a scope having a solid image sensor provided at a distal end thereof to generate image-pixel signals, and an image-signal processing unit that produces a video signal on the basis of the image-pixel signals, wherein a peak-to-peak level of the synchronizing-signal component of the video signal can be manually and easily changed such that various types of TV monitors can accept the video signal.

In accordance with an aspect of the present invention, there is provided an electronic endoscope system including a scope having a solid image sensor provided at a distal end thereof to generate image-pixel signals, and an image-signal processing unit that produces a video signal based on the image-pixel signals. In the electronic endoscope system, an alteration alters a peak-to-peak level of a synchronizing-signal component of the video signal, and an manual setting system manually operates the alteration system to perform the alteration of the peak-to-peak level of the synchronizing-signal component.

Preferably, the manual setting system is constituted such that the alteration of the peak-to-peak level of the synchronizing-signal component is stepwise performed by the alteration system.

The alteration system may comprise a multiplier, and the manual setting system comprises a manual digital switch that produces code data, a multiplier-factor of the multiplier being altered in accordance with the code data produced by the manual digital switch.

Optionally, the alteration system comprises a voltage-controlled amplifier, an amplification factor of which is altered in accordance with a level of a voltage signal applied thereto. In this case, the manual setting system may comprise a manual digital switch that produces code data, and a voltage signal generator that generates the voltage signal such that the level of the voltage signal is altered in accordance with the code data produced by the manual digital switch.

In the alteration system comprising the voltage-controlled amplifier, the manual setting system may comprise a storage system that stores voltage data, a voltage signal generator that generates the voltage signal such that the level of the voltage signal is altered in accordance with the voltage data stored in the storage system. In this case, a manual-altering system that manually alters the voltage data stored in the storage system. Preferably, the storage system comprises a non-volatile memory, such as an electrically erasable programmable read-only memory.

In an electronic endoscope system according to another aspect of the present invention, a first alteration system alters a peak-to-peak level of a synchronizing-signal component of the first video signal, a first manual setting system manually operates the first alteration system to perform the alteration of the peak-to-peak level of the synchronizing-signal component of the first video signal, a second alteration system alters a peak-to-peak level of a synchronizing-signal component of the second video signal, and a second manual setting system manually operates the second alteration system to perform the alteration of the peak-to-peak level of the synchronizing-signal component of the second video signal.

BRIEF DESCRIPTION OF THE DRAWINGS

The object and other objects of the present invention will be better understood from the following descriptions, with reference to the accompanying drawings, in which.

DESCRIPTION OF THE PREFERRED EMBODIMENTS

Figure 1:
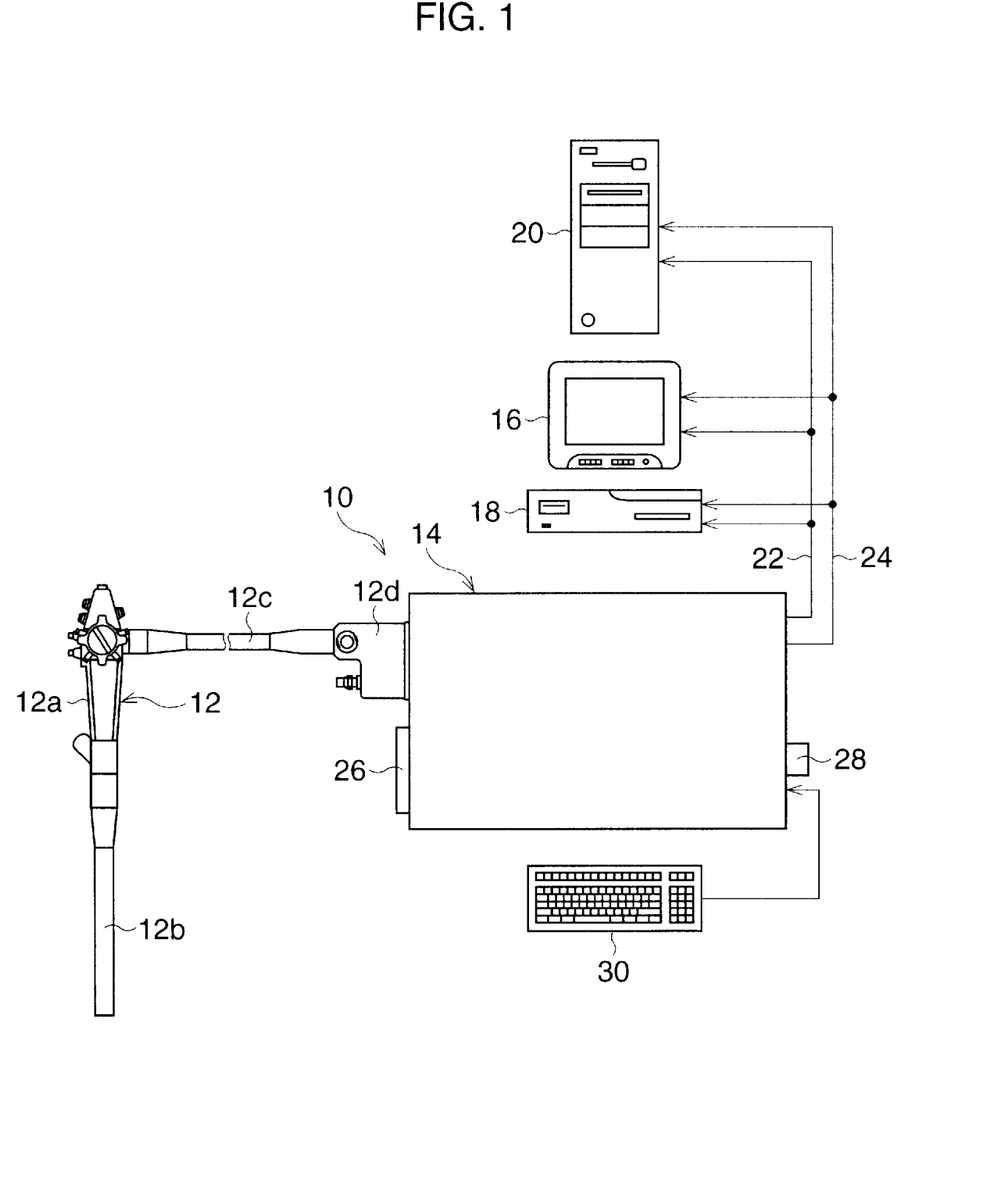
FIG. 1 is a schematic view entirely showing an electronic endoscope system according to the present invention.

FIG. 1 schematically shows an electronic endoscope system according to the present invention. The electronic endoscope 10 comprises an elongated scope 12 formed from a rigid conduit 12a and a flexible conduit 12b and having a flexible cable 12c extending from the rigid conduit 12a, and terminating with a connector 12d. The electronic endoscope 10 also comprises an image-signal processing unit 14 to which the scope 12 is detachably connected through the intermediary of the flexible cable 12c and the connector 12d. The scope 12 is a representative of various types of scope, used for bronchial, esophageal, gastro, colon, etc. inspections, and these various types of scope use the image-signal processing unit 14 in common.

The flexible conduit 12b of the scope 12 has a solid image sensor (not shown), such as a CCD (charge-coupled-device) image sensor, at the distal end thereof, and the CCD image sensor is associated with an objective lens system (not shown). When the connection is established between the scope 12 and the image-signal processing unit 14, the CCD image sensor is electrically connected to an image-signal processor in the image-signal processing unit 14.

Also, the scope 12 includes a flexible optical light guide extended therethrough and formed as a bundle of optical fibers. The optical light guide terminates with a light-radiating end face at the distal end of the flexible conduit 12b of the scope 12, and is associated with a lighting lens system (not shown) provided thereat. When the connection is established between the scope 12 and the image-signal processing unit 14, the proximal end of the optical light guide is optically connected to a light source device provided in the image-signal processing unit 14, whereby the light, emitted from the light source device, radiates as an illuminating-light from the light-radiating end face of the optical light guide.

When the flexible conduit 12b of the scope 12 is inserted in the body of a patient, an illuminated object is focussed as an optical image on a light-receiving surface of the CCD image sensor, by the objective lens system associated therewith. The focussed optical image is converted into analog image-pixel signals by the CCD image sensor, and the analog image-pixel signals are read from the CCD image sensor by a CCD driver provided in the connector 12d of the scope 12. The signals are then fed to the image-signal processor provided in the image-signal processing unit 14. In the image-signal processor, the image-pixel signals are suitably processed to produce a video signal, which is then fed from the image-signal processor to a TV monitor 16, thereby reproducing the object image on the TV monitor 16 in accordance with the video signal. Also, as shown in FIG. 1, the video signal may be fed to peripheral equipment, such as a video printer 18, an image-processing computer 20 and so on.

In this embodiment, to reproduce the image on the TV monitor 16 as a color image, an RGB field sequential-type color imaging method is incorporated in the electronic endoscope system. Thus, in the image-signal processor, the video signal is produced as a component-type color video signal composed of red, green and blue video signal components and a compound-synchronizing-signal component which includes various synchronizing signals, such as a horizontal synchronizing signal, a vertical synchronizing signal and so on. In FIG. 1, a signal cable 22 is provided for feeding the red, green and blue video signal components, and a signal cable 24 is provided for feeding the compound-synchronizing-signal component.

The image-signal processing unit 14 includes a housing with a front switch panel 26 attached to the front wall thereof, and various switches and indicator-lamps are provided in the front switch panel 26. Also, the housing has a rear switch panel 28 attached to the rear wall thereof, and switches are provided in the rear switch panel 28 to change a peak-to-peak level of the compound-synchronizing-signal component output from the image-signal processor. Also, as shown in FIG. 1, a keyboard 30 is connected to the image-signal processing unit 14 as an input device.

Figure 2:
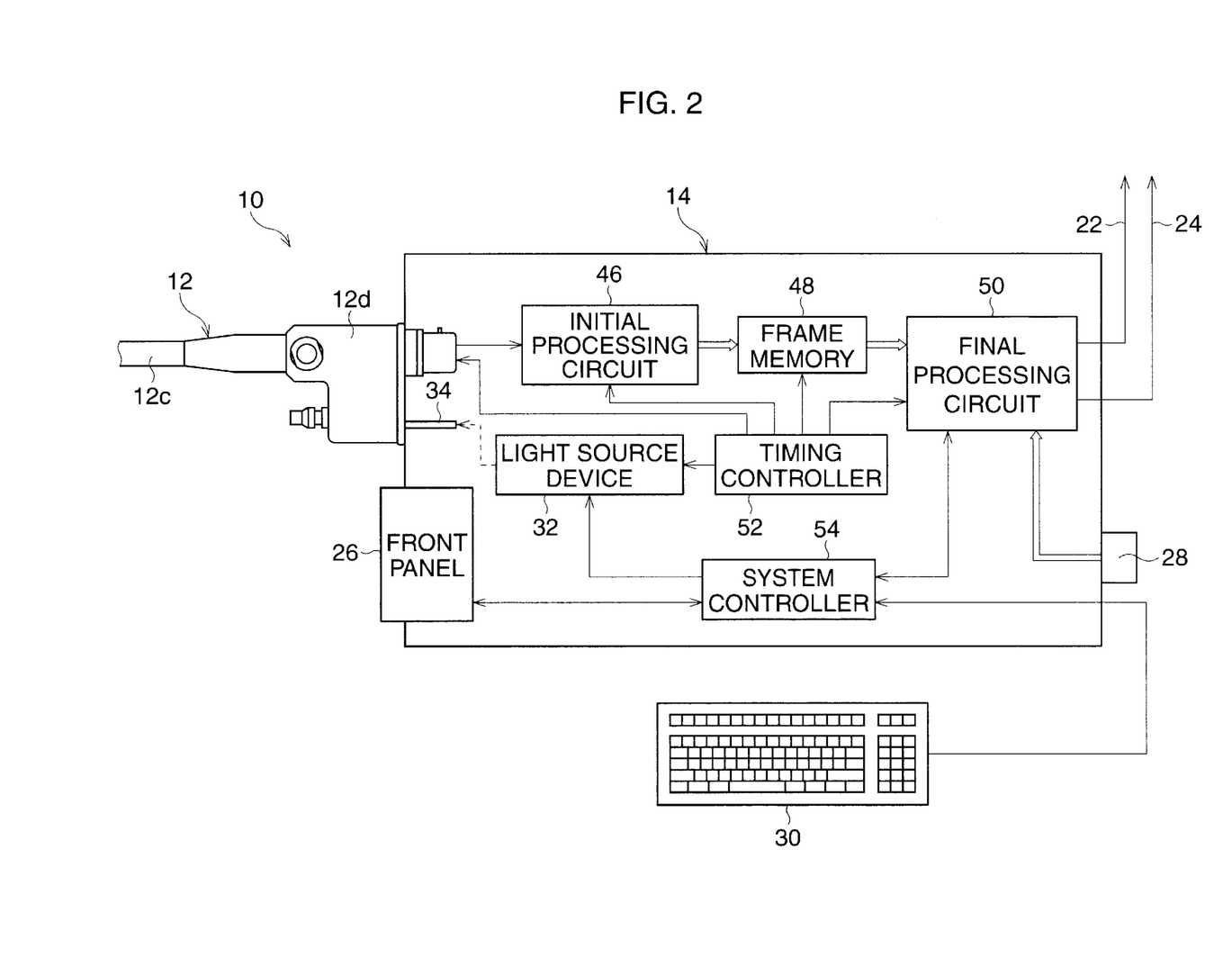
FIG. 2 is a schematic block diagram of an image-signal processing unit of the electronic endoscope.

FIG. 2 schematically shows a block diagram of the image-signal processing unit 14.

The aforementioned light source device, provided in the image-signal processing unit 14, is indicated by reference 32. The optical light guide extending through the scope 12 has a rigid optical plug 34 joined to the proximal end thereof, such that the proximal end of the optical light guide is optically connected to the light source device 32 via the rigid optical plug 34. The rigid optical plug 34 is securely supported by the connector 12d, and is optically connected to the light source device 32 when the connector 12d is inserted in a socket (not shown) provided on the front wall of the housing of the image-signal processing unit 14. Note, in FIG. 2, the optical connection between the light source device 32 and the rigid optical plug 34 is represented by an arrow-headed broken line for convenience.

Figure 3:
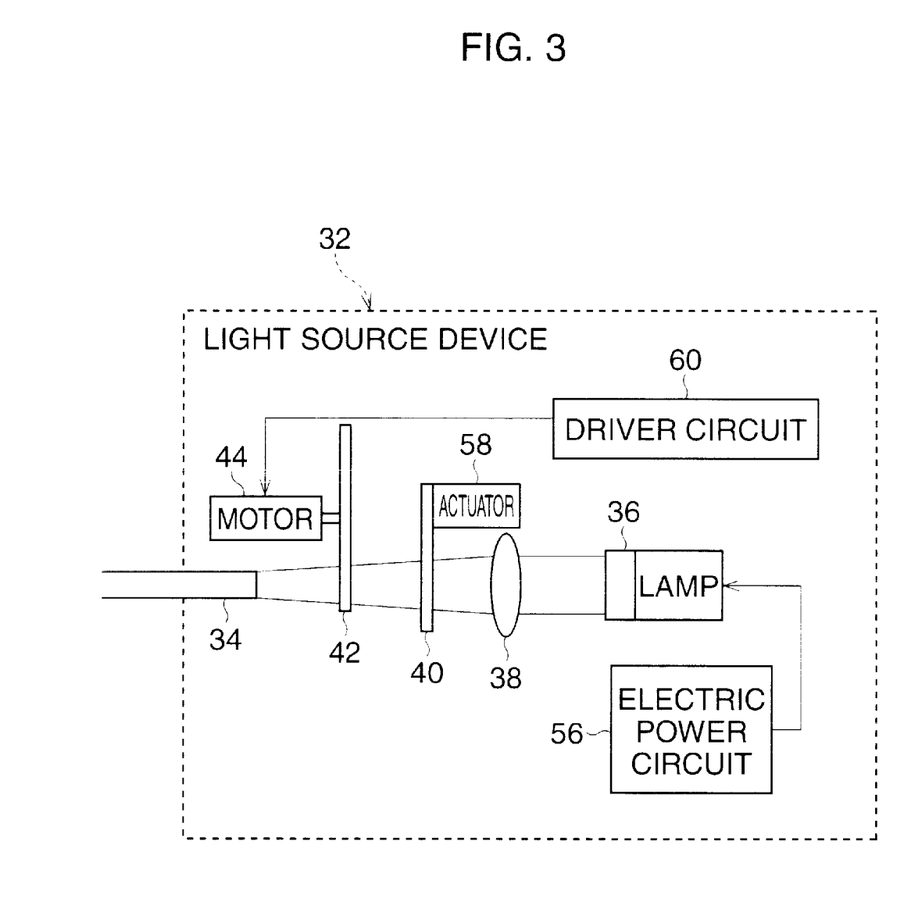
FIG. 3 is a schematic block diagram of a light source device provided in the image-signal processing unit.

As shown in FIG. 3, the light source device 32 includes a white lamp 36, such as a halogen lamp, a xenon lamp or the like, for emitting white light, a condenser lens 38 for converging the emitted white light on the free end face of the rigid optical plug 34, and a diaphragm 40 for regulating an amount of white light directed from the white lamp 18 to the free end face of the rigid optical plug 34, i.e. an amount of the illuminating-light radiating from the distal end of the optical light guide.

As mentioned above, since the RGB field sequential-type color imaging method is incorporated in the electronic endoscope system, a rotary color filter disk 42 is interposed between the diaphragm 38 and the free end face of the rigid optical plug 34. The rotary RGB color filter disk 42 has three sector-shaped color filters, i.e. red, green and blue filters, and these color filters are circumferentially and uniformly arranged such that three centers of the color filters are spaced from each other at regular angular-intervals of 120 degrees, with a sector area between two adjacent color filters serving as a light-shielding area.

The rotary RGB color filter disk 42 is rotated by a suitable electric motor 44, such as a servo-motor, a stepping motor or the like, at a given rotational frequency in accordance with a used image-reproduction method, such as NTSC, PAL and so on, whereby the object to be captured by the CCD image sensor is sequentially illuminated by red light, green light and blue light. Namely, a red optical image, a green optical image and a blue optical image are sequentially and cyclically focused on the light-receiving surface of the CCD image sensor.

Note, in the NTSC system, the rotational frequency of the color filter disk 42 is 30 Hz, and, in the PAL system, the rotational frequency of the color filter disk 42 is 25 Hz.

Each of the red, green and blue optical images is sequentially converted into a frame of monochromatic (red, green, blue) analog image-pixel signals by the CCD image sensor, and the monochromatic (red, green, blue) analog image-pixel signals are successively read from the CCD image sensor over consecutive light-shielding time periods corresponding to the light-shielding areas between two adjacent color filters. The monochromatic analog image-pixel signals are then fed to the image-signal processor provided in the image-signal processing unit 14.

As shown in FIG. 2, the image-signal processor, provided in the image-signal processing unit 14, includes an initial processing circuit 46, a frame memory 48 and a final processing circuit 50, and is sequentially and systematically operated in accordance with various series of clock pulses output from a timing controller 52. Note, the reading of the monochromatic analog image-pixel signals from the CCD image sensor is performed by operating the CCD driver in accordance with clock pulses output from the timing controller 52 which is operated under control of the system controller 54.

The monochromatic analog image-pixel signals, fed to the image-signal processor, are suitably processed in the initial processing circuit 46 under control of the timing controller 52. For example, the monochromatic analog image-pixel signals are subjected to white-balance correction, gamma-correction, profile-enhancing and so on. Then, the processed monochromatic analog image-pixel signals are converted into monochromatic digital image-pixel signals by an analog-to-digital converter provided in the initial processing circuit 46.

The monochromatic digital image-pixel signals are temporarily stored in the frame memory 48. In the frame memory 48, three memory sections are defined for the storage of red, green and blue digital image-pixel signals, respectively. In short, the monochromatic digital image-pixel signals are stored in a memory section, defined in the frame memory 48, that corresponds to the image pixel color.

While the monochromatic digital image-pixel signals are successively stored in the frame memory 48, the respective red, green and blue digital image-pixel signals are simultaneously read from the three frame memory sections of the frame memory 48 in a series of timing clock pulses output from the timing controller 52, and are output to the final processing circuit 50, as red, green and blue digital video signal components, respectively. The timing controller 52 also produces a compound-synchronizing-signal component, and outputs it to the final processing circuit 50. Thus, the component-type video signal is produced in the final processing circuit 50, and is suitably processed therein. Thereafter, the component-type video signal is output as an analog component-type video signal from the final processing circuit 50 to the TV monitor 16, as stated in detail hereinafter.

Note that the system controller 54 is constituted as a microcomputer, used to control the electronic endoscope system as a whole, comprising a central processing unit (CPU), a read-only memory (ROM) for storing programs and constants, a random-access memory (RAM) for storing temporary data, and an input/output interface circuit (I/O).

For example, in FIG. 3, an electric power circuit 56 for electrically energizing the white light 36 is operated under control of the system controller 54. Also, an actuator 58 for driving the diaphragm 40 is operated under control of the system controller 54 such that the brightness of the display of the TV monitor 16 is constant. Further, a driver circuit 60 for driving the motor 44 of the rotary RGB color filter disk 43 is operated under control of the system controller 54.

Figure 4:
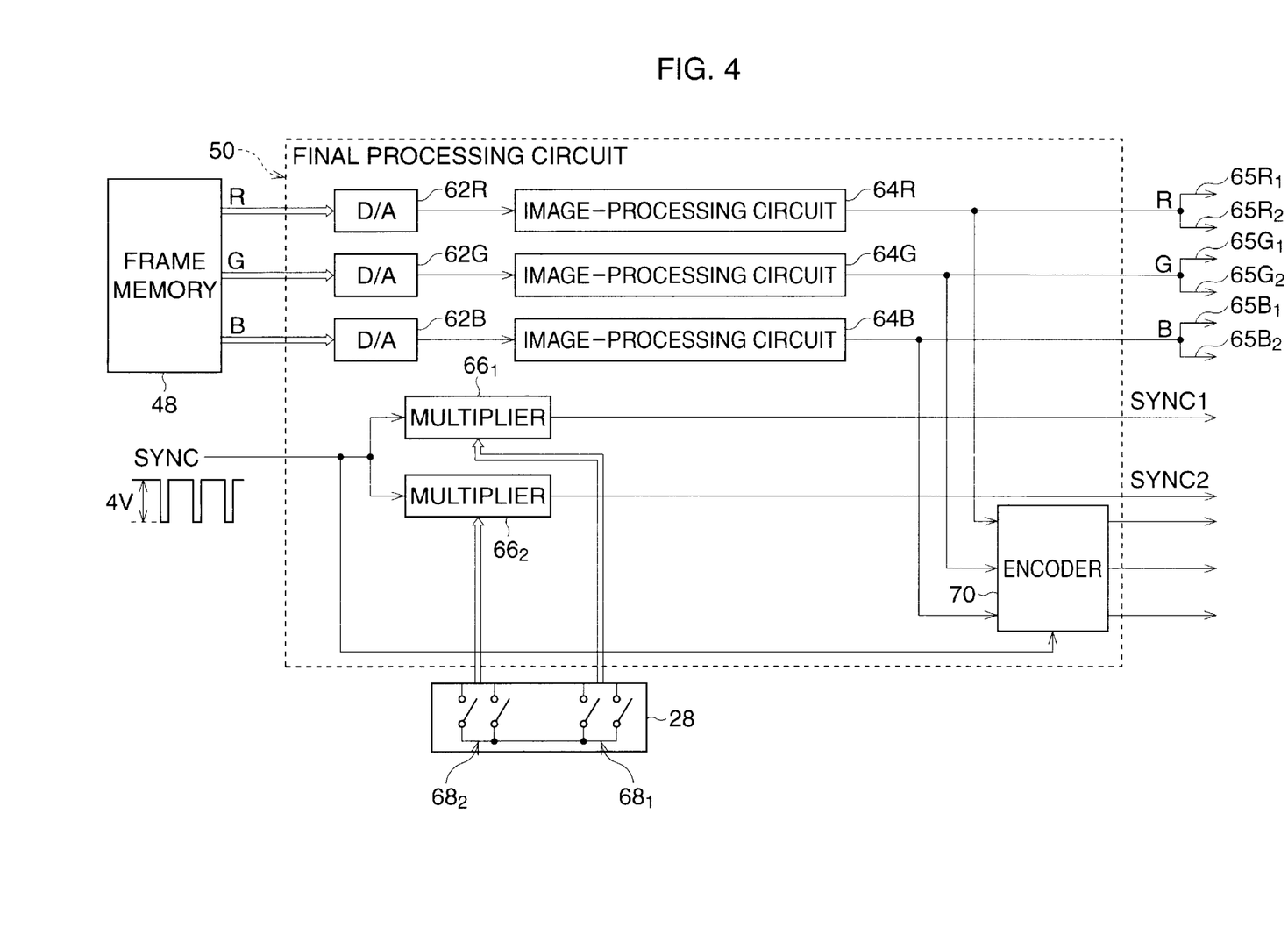
FIG. 4 is a schematic block diagram of a final processing circuit of an image-signal processor provided in the image-signal processing unit.

FIG. 4 shows a block diagram of the final processing circuit 50. As is apparent from this drawing, the final processing circuit 50 includes three digital-to-analog (D/A) converters 62R, 62G and 62B and three image-processing circuits 64R, 64G and 64B. The respective digital red, green and blue video signal components (R, G and B), output from the frame memory 48, are converted into analog red, green and blue video signal components by the D/A converters 62R, 62G and 62B, and the respective analog red, green and blue video signal components are suitably processed in the image-processing circuits 64R, 64G and 64B. For example, the red, green and blue video signal components (R, G and B) are subjected to a color-balance processing, a noise-filtering processing and so on. The processed red, green and blue video signal components are output from the image-signal processing unit 14.

As shown in FIG. 4, each output-signal line extending from the image-processing circuits 64R, 64G and 64B terminates at a fork having two output terminals ($65R_1$, $65R_2$; $65G_1$, $65G_2$; $65B_1$, $65B_2$), so that two sets of red, green and blue video signal components (R, G and B) are output from the image-processing circuits 64R, 64G and 64B.

The final processing circuit 50 also includes a first multiplier $66_1$ and a second multiplier $66_2$, and the compound-synchronizing-signal component (SYNC), output from the timing controller 52, is input to the first and second multipliers $66_1$ and $66_2$. In the timing controller 52, the compound synchronizing-signal component (SYNC) is produced as a voltage signal exhibiting a peak-to-peak level of 4 volts, and each of the first and second multipliers $66_1$ and $66_2$ is provided to discretely change the peak-to-peak level of the compound-synchronizing-signal component. In FIG. 4, the compound-synchronizing-signal component, output from the first multiplier $66_1$, is indicated by reference SYNC1, and the compound-synchronizing-signal component, output from the second multiplier $66_2$, is indicated by reference SYNC2.

In short, in this embodiment, the final processing circuit 50 is constituted to output two sets of component-type color video signals: a first component-type color video signal composed of the primary-color video signal components (R, G and B) and the synchronizing-signal component (SYNC1); and a second component-type color video signal composed of the primary-color video signal components (R, G and B) and the synchronizing-signal component (SYNC2).

A multiplier-factor set in each multiplier ($66_1$, $66_2$) can be manually changed. To this end, a first setting-switch $68_1$ and a second setting-switch $68_2$ are provided in the rear switch panel 28 to change the settings of the multiplier-factors in the multipliers $66_1$ and $66_2$, respectively. In this embodiment, each of the first and second setting-switches $68_1$ and $68_2$ is formed as a digital switch, called a "DIP switch". Each of the first and second DIP switches $68_1$ and $68_2$ includes two ON/OFF switch elements for producing 2-bit code data. Namely, one of the ON/OFF switch elements represents a low-order bit of the 2-bit code data, and the other ON/OFF switch element represents a high-order bit of the 2-bit code data. The setting of the multiplier-factor is changed in each multiplier ($66_1$, $66_2$) by manually operating the ON/OFF switch elements of the corresponding DIP switch ($68_1$, $68_2$).

For example, each of the multiplier $66_1$ and $66_2$ is formed as a signal-amplifying circuit having a variable resistance, a resistance value of which is regulated in accordance with the 2-bit code data set by the DIP switch ($68_1$, $68_2$). Namely, the multiplier-factor of each multiplier corresponds to an amplification factor of the signal-amplifying circuit, and is altered in accordance with the variation of the resistance value of the variable resistance.

In this embodiment, an alteration of the setting of the multiplier-factor is performed as shown in the following TABLE I:

TABLE I

| 2-BIT CODE DATA | MULTIPLIER-FACTOR | VOLTAGE LEVEL (volts) |
|---|---|---|
| [00] | 1.00 | 4 |
| [01] | 0.75 | 3 |
| [10] | 0.50 | 2 |
| [11] | 0.25 | 1 |

For example, when both the ON/OFF switch elements are manually turned OFF, each DIP switch ($68_1$, $68_2$) produces and outputs 2-bit code data [00] to the multiplier ($66_1$, $66_2$), whereby a multiplier-factor of 1.00 is set in the multiplier ($66_1$, $66_2$). In this case, the peak-to-peak level of the compound-synchronizing-signal component is maintained at 4 volts as the multiplier-factor is 1.00.

Also, when the ON/OFF switch element representing the low-order bit is turned ON, and when the ON/OFF switch element representing the high-order bit is turned OFF, each DIP switch ($68_1$, $68_2$) produces and outputs 2-bit code data [01] to the multiplier ($66_1$, $66_2$), whereby a multiplier-factor of 0.75 is set. In this case, the peak-to-peak level of the compound-synchronizing-signal component is changed from 4 volts to 3 volts by the multiplier ($66_1$, $66_2$) as the multiplier-factor is 0.75.

Further, when the ON/OFF switch element representing the low-order bit is turned OFF, and when the ON/OFF switch element representing the high-order bit is turned ON, each DIP switch ($68_1$, $68_2$) produces and outputs 2-bit code data [10] to the multiplier ($66_1$, $66_2$), whereby a multiplier-factor of 0.50 is set. In this case, the peak-to-peak level of the compound-synchronizing-signal component is changed from 4 volts to 2 volts by the multiplier ($66_1$, $66_2$) as the multiplier-factor is 0.50.

When both the ON/OFF switch elements are manually turned ON, each DIP switch ($68_1$, $68_2$) produces and outputs 2-bit code data [11] to the multiplier ($66_1$, $66_2$), whereby a multiplier-factor of 0.25 is set. In this case, the peak-to-peak level of the compound-synchronizing-signal component is changed from 4 volts to 1 volt by the multiplier ($66_1$, $66_2$) as the multiplier-factor is 0.25.

Accordingly, when a domestic TV monitor is used in the electronic endoscope system, it is possible to change the peak-to-peak level (4 volts) of the compound-synchronizing-signal component to either 1, 2 or 3 volts so that the compound-synchronizing-signal component is accepted by the domestic TV monitor.

Note, in FIG. 4, reference 70 indicates a color encoder producing a composite-type color video signal and/or an S-video signal from the component-type color video signal (R, G, B, SYNC), and each of these color video signals is output from the color encoder 70 to peripheral equipment, such as a video tape recorder, if necessary.

Figure 5:
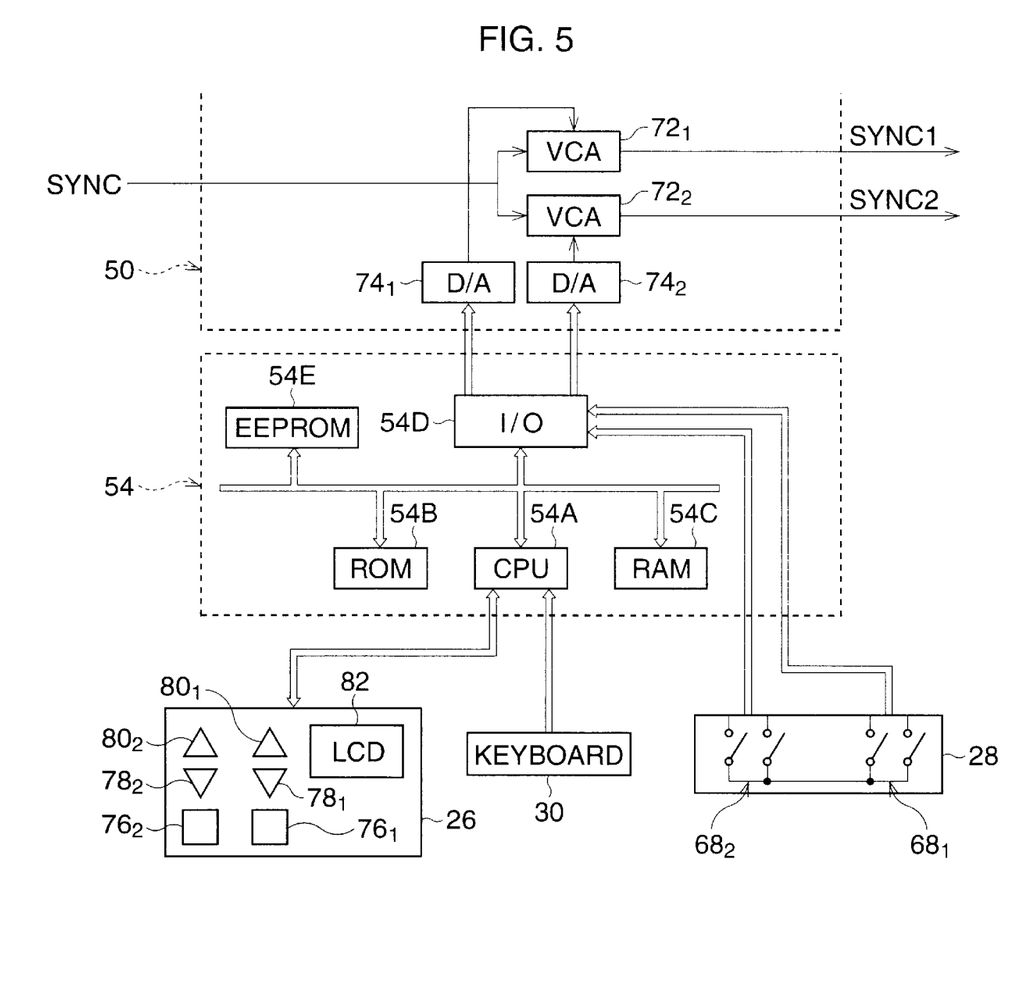
FIG. 5 is a schematic block diagram showing a modified part of the final processing circuit shown in FIG. 4, together with a system controller, a rear panel, a keyboard and a front panel.

FIG. 5 partially shows a modification of the final processing circuit 50, in which two voltage-controlled amplifiers (VCA) $72_1$ and $72_2$ are substituted for the multipliers $66_1$ and $66_2$. As is well known, each of the VCA $72_1$ and $72_2$ is constituted such that the amplification factor is altered in accordance with the level of input voltage applied.

In the modified embodiment, alteration of the input voltage to the VCA ($72_1$, $72_2$) is performed by the system controller 54, in accordance with the 2-bit code data output from a corresponding DIP switch ($68_1$, $68_2$). To this end, the respective VCA's $72_1$ and $72_2$ are provided with digital-to-analog (D/A) converters $74_1$ and $74_2$. Note that, in FIG. 5, the CPU, ROM, RAM and I/O of the system controller 54 are indicated by references 54A, 54B, 54C and 54D, respectively. As is apparent from FIG. 5, the D/A converters $72_1$ and $72_2$ are connected to output ports of I/O 54D, and the DIP switches $68_1$ and $68_2$ are connected to input ports of the I/O 54D.

Figure 6:
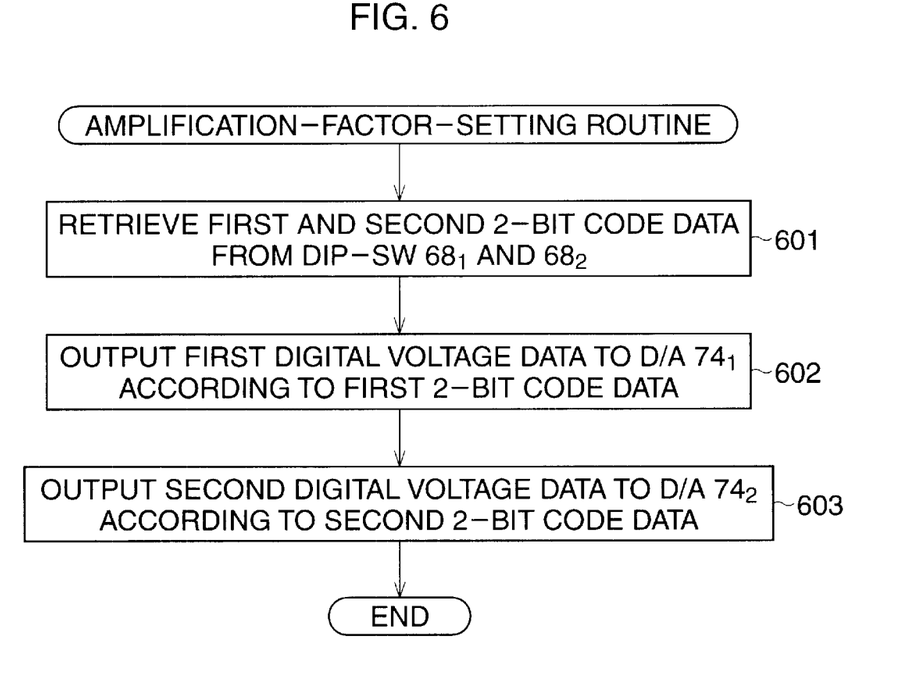
FIG. 6 is a flowchart of an amplification-factor-setting routine executed in the system controller of the image-signal processing unit.

FIG. 6 shows a flowchart of an amplification-factor-setting routine for setting an amplification factor in each VCA ($72_1$, $72_2$). Note that, the amplification-factor-setting routine is only executed once by the system controller 54 as a part of the initialization-routine of the image-signal processing unit 14 whenever the main power switch (not shown), provided on the front panel 26, is turned ON.

At step 601, first and second 2-bit code data are retrieved from the DIP switches $68_1$ and $68_2$, and are temporarily stored in the RAM 54C.

At step 602, first digital voltage data is output from the I/O 54D to the D/A converter $74_1$ in accordance with the first 2-bit code data retrieved from the DIP switch $68_1$. The D/A converter $74_1$ converts the first digital voltage data into a first analog voltage exhibiting a first voltage level corresponding to the first 2-bit code data, and the first analog voltage is applied to the VCA $72_1$, whereby the amplification factor of the VCA $72_{12}$ is set in accordance with the first analog voltage level.

At step 603, second digital voltage data is output from the I/O 54D to the D/A converter $74_2$, in accordance with the second 2-bit code data retrieved from the DIP switch $68_2$. The D/A converter $74_2$ converts the second digital voltage data into a second analog voltage exhibiting a second voltage level corresponding to the second 2-bit code data, and the second analog voltage is applied to the VCA $72_2$, whereby the amplification factor of the VCA $72_2$ is set in accordance with the second analog voltage level.

The different settings of the amplification factor for each VCA ($72_1$, $72_2$) is shown in the following TABLE II:

TABLE II

| 2-BIT CODE DATA | ANALOG VOLTAGE | AMPLIFICATION FACTOR | VOLTAGE LEVEL (volts) |
|---|---|---|---|
| [00] | $V_3$ | 1.00 | 4 |
| [01] | $V_2$ | 0.75 | 3 |
| [10] | $V_1$ | 0.50 | 2 |
| [11] | $V_0$ | 0.25 | 1 |

For example, when 2-bit code data [00] is retrieved from each DIP switch ($68_1$, $68_2$), an analog voltage $V_3$ is applied by the D/A converter ($74_1$, $74_2$) to the VCA ($72_1$, $72_2$), whereby an amplification factor of 1.00 is set in the VCA ($72_1$, $72_2$) In this case, the peak-to-peak level of the compound-synchronizing-signal component is maintained at 4 volts as the amplification factor is 1.00.

Also, when 2-bit code data [01] is retrieved from each DIP switch ($68_1$, $68_2$), an analog voltage $V_2$ is applied by the D/A converter ($74_1$, $74_2$) to the VCA ($72_1$, $72_2$), whereby an amplification factor of 0.75 is set in the VCA ($72_1$, $72_2$). In this case, the peak-to-peak level of the compound-synchronizing-signal component is changed from 4 volts to 3 volts as the amplification factor is 0.75.

Further, when 2-bit code data [10] is retrieved from each DIP switch ($68_1$, $68_2$), an analog voltage $V_1$ is applied by the D/A converter ($74_1$, $74_2$) to the VCA ($72_1$, $72_2$), whereby an amplification factor of 0.50 is set in the VCA ($72_1$, $72_2$). In this case, the peak-to-peak level of the compound-synchronizing-signal component is changed from 4 volts to 2 volts as the amplification factor is 0.50.

When 2-bit code data [11] is retrieved from each DIP switch ($68_1$, $68_2$), an analog voltage $V_0$ is applied by the D/A converter ($74_1$, $74_2$) to the VCA ($72_1$, $72_2$), whereby an amplification factor of 0.50 is set in the VCA ($72_1$, $72_2$). In this case, the peak-to-peak level of the compound-synchronizing-signal component is changed from 4 volts to 1 volts by the VCA ($72_1$, $72_2$) as the amplification factor is 0.25.

In the modified embodiment shown in FIG. 5, the DIP switches $68_1$ and $68_2$ may be replaced by a non-volatile memory, such as an electrically erasable programmable read-only memory (EEPROM) 54E, provided in the system controller 54, which stores first and second digital voltage data to be output to the D/A converters $74_1$ and $74_2$, respectively. Each of the first and second digital voltage data corresponds to one of the analog voltages $V_3$, $V_2$, $V_1$ and $V_0$, and is alterable in the EEPROM 54E, using the keyboard 30.

Figure 7:
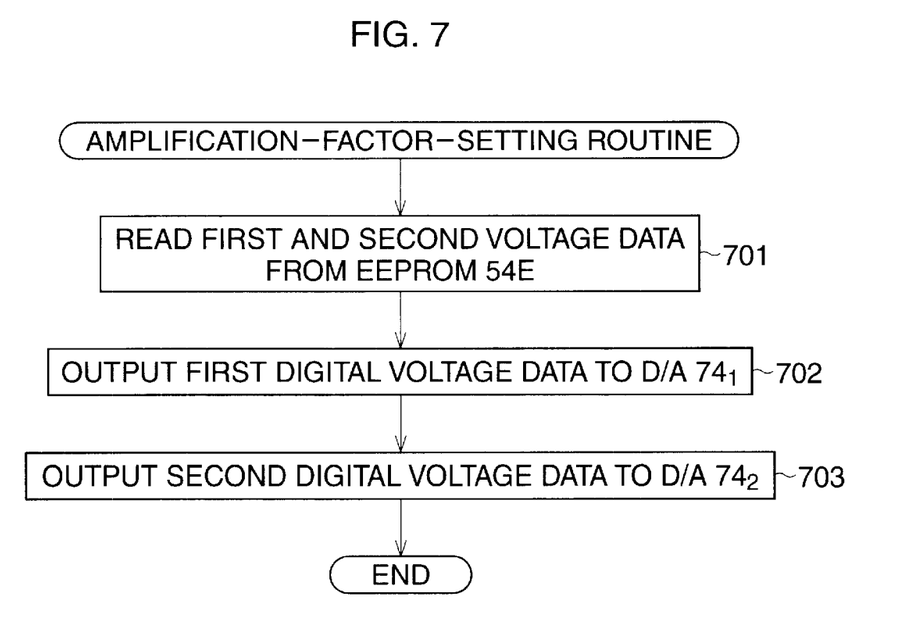
FIG. 7 is a flowchart of another amplification-factor-setting routine executed in the system controller of the image-signal processing unit.

FIG. 7 shows a flowchart of an amplification-factor-setting routine for setting the amplification factor in each VCA ($72_1$, $72_2$) when the EEPROM 54E is substituted for the DIP switches $68_1$ and $68_2$. Note that, similar to the routine of FIG. 6, this amplification-factor-setting routine is only executed once by the system controller 54 as a part of an initialization-routine of the image-signal processing unit 14 whenever the main power switch, provided on the front panel 26, is turned ON.

At step 701, the first and second digital voltage data are read from the EEPROM 54E. Then, at step 702, the first digital voltage data is output from the I/O 54D to the D/A converter $74_1$, in which the first digital voltage is converted into a first analog voltage and is applied to the VCA $72_1$, wherein the amplification factor of the VCA $72_1$ is set in accordance with the first analog voltage level. Subsequently, at step 703, the second digital voltage data is output from the I/O 54D to the D/A converter $74_2$, in which the second digital voltage is converted into a second analog voltage and is applied to the VCA $72_2$, wherein the amplification factor of the VCA $72_2$ is set in accordance with the second analog voltage level.

Figure 8:
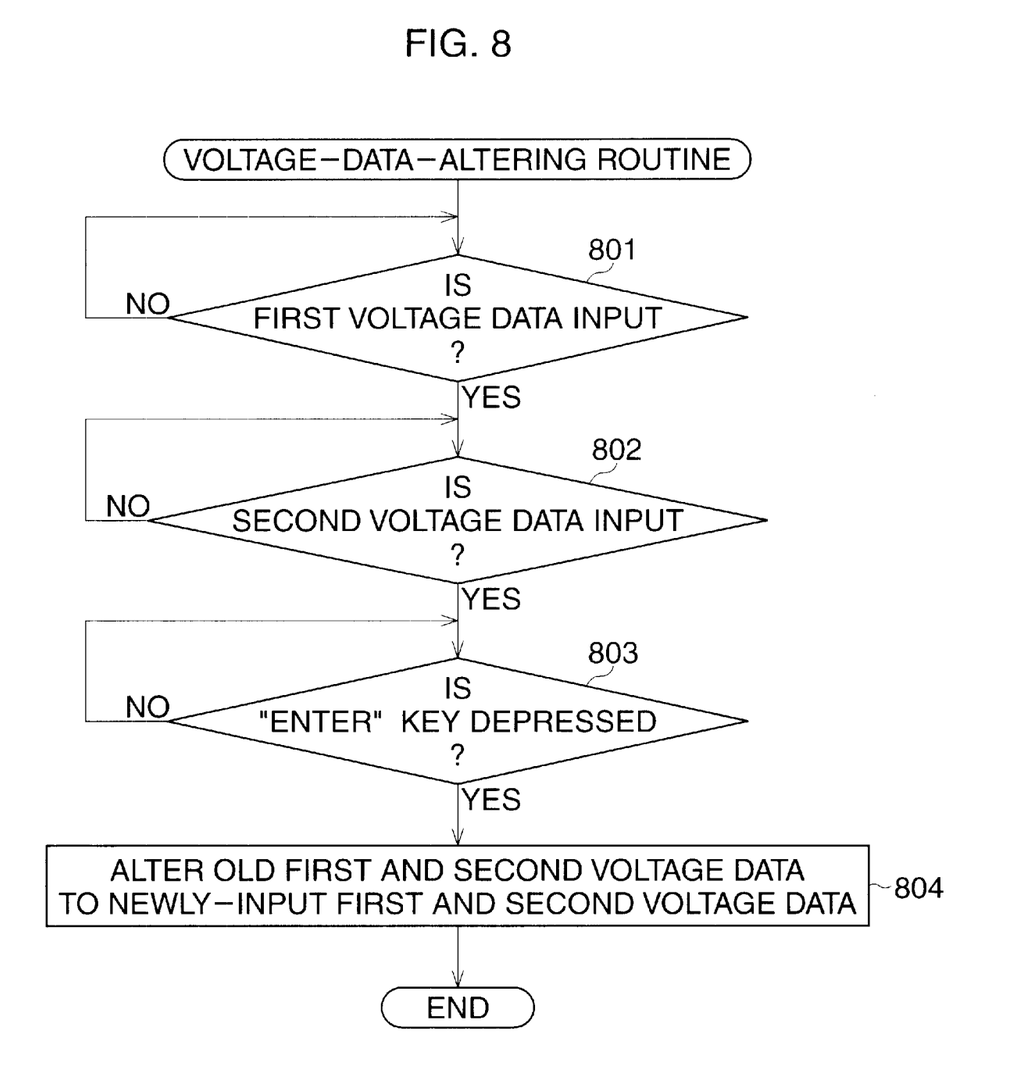
FIG. 8 is a flowchart of a voltage-data-altering routine executed in the system controller of the image-signal processing unit.

FIG. 8 shows a flowchart of a voltage-data-altering routine for altering the first and second digital voltage data in the EEPROM 54E. The voltage-data-altering routine is executed by a predetermined function key on the keyboard 30. Also, preferably, a window for altering the first and second voltage data in the EEPROM 54E may be displayed on the TV monitor 16.

At step 801, it is monitored whether first voltage data to be output to the D/A converter $74_1$ is input to the system controller 54, using the keyboard. When the inputting of the first voltage data is confirmed, the control proceeds to step 802, in which it is monitored whether second voltage data to be output to the D/A converter $74_2$ is input to the system controller 54, using the keyboard. When the inputting of the second voltage data is confirmed, the control proceeds to step 803.

At step 803, it is monitored whether an "Enter" key on the keyboard 30 is depressed. When the depression of the "Enter" key is confirmed, the control proceeds to step 804, in which the old first and second voltage data, stored in the EEPROM 54E, are altered to the newly-input first and second voltage data. Namely, in the EEPROM 54E, the newly-input first and second voltage data overwrite the old first and second voltage data.

At steps 801 and 802, each of the first and second voltage data may be input to the system controller 54 as a numerical value representing a peak-to-peak level of the compound-synchronizing-signal component (SYNC).

For example, when the first voltage data is input as a numerical value "3" representing the peak-to-peak level of 3 volts of the compound-synchronizing-signal component (SYNC), the newly-input first voltage data overwrites the old first voltage data in the EEPROM 54E (step 804). Thus, in the execution of the amplification-factor-setting routine, the newly-input first voltage data is converted into the analog voltage $V_2$ by the D/A converter $74_1$ (step 702), and thus an amplification factor of 0.75 is set in the VCA $72_1$ (cf. TABLE II). Therefore, the peak-to-peak level of the compound-synchronizing-signal component (SYNC) is changed from 4 volts to 3 volts by the VCA $72_1$.

Similarly, when the second voltage data is input as a numerical value "2" representing the peak-to-peak level of 2 volts of the compound-synchronizing-signal component (SYNC), the newly-input second voltage data overwrites the old second voltage data in the EEPROM 54E (step 804). Thus, in the execution of the amplification-factor-setting routine, the newly-input second voltage data is converted into the analog voltage $V_1$ by the D/A converter $74_2$ (step 703), and an amplification factor of 0.50 is set in the VCA $72_2$ (cf. TABLE II). Therefore, the peak-to-peak level of the compound-synchronizing-signal component (SYNC) is changed from 4 volts to 2 volts.

Optionally, it is possible to alter the first and second digital voltage data, stored in the EEPROM 54E, using switches $76_1$, $76_2$, $78_1$, $78_2$, $80_1$, and $80_2$ provided on the front panel 26 for the aforesaid color-balance processing (FIG. 5).

The switch $76_1$ serves as a red-regulation-enabling switch which is turned ON by a depression and which is turned OFF when being released from the depression. Namely, the ON-state of switch $76_1$ is continued while being depressed. The respective switches $78_1$ and $80_1$ serve as a red-emphasizing switch and a red-weakening switch, each of which is instantaneously turned ON only when being subjected to a depression. When the red-regulation-enabling switch $76_1$ is depressed once and turned ON, the red-emphasizing switch $78_1$ and the red-weakening switch $80_1$ are enabled. When the red-regulation-enabling switch $76_1$ is depressed again and turned ON, both the red-emphasizing switch $78_1$ and the red-weakening switch $80_1$ are disabled.

While the red-emphasizing switch $78_1$ and the red-weakening switch $80_1$ are enabled, red is increasingly emphasized in a color image, displayed on the TV monitor 16, by each depression of the red-emphasizing switch $78_1$, and the red is increasingly weakened in the color image by each depression of the red-weakening switch $80_1$. Note that, for example, the switches $76_1$, $78_1$ and $80_1$ are utilized to alter the first voltage data, stored in the EEPROM, for the D/A converter $74_1$ as stated in detail hereinafter.

The switch $76_2$ serves as a blue-regulation-enabling switch, which is turned ON by a depression and which is turned OFF when being released from the depression. Namely, the ON-state of switch $76_2$ is continued while being depressed. The respective switches $78_2$ and $80_2$ serve as a blue-emphasizing switch and a blue-weakening switch, each of which is instantaneously turned ON only when being subjected to a depression. When the blue-regulation-enabling switch $76_2$ is depressed once and turned ON, the blue-emphasizing switch $78_2$ and the blue-weakening switch $80_2$ are enabled. When the blue-regulation-enabling switch $76_2$ is depressed again and turned ON, the blue-emphasizing switch $78_2$ and the blue-weakening switch $80_2$ are disabled.

While the blue-emphasizing switch $78_2$ and the blue-weakening switch $80_2$ are enabled, blue is increasingly emphasized in the color image, displayed on the TV monitor 16, by each depression of the blue-emphasizing switch $78_2$, and the blue is increasingly weakened in the color image by each depression of the blue-weakening switch $78_2$. Note that the switches $76_2$, $78_2$ and $80_2$ are utilized to alter the second voltage data, stored in the EEPROM, for the D/A converter $74_2$, as stated in detail hereinafter.

In order to utilize the switches $76_1$, $76_2$, $78_1$, $78_2$, $80_1$ and $80_2$ for the alteration of the first and second digital voltage data, stored in the EEPROM 54E, whenever either the switch $76_1$ or $76_2$ is turned ON, it is monitored whether the ON-state of each switch ($76_1$, $76_2$) is continued over a predetermined time, for example, 4 sec, and the continuous ON-state of the switch ($76_1$, $76_2$) over the time of 4 sec enables the switches $78_1$, $78_2$, $80_1$ and $80_2$ to be used to alter the first and second digital voltage data, stored in the EEPROM 54E.

Figure 9:
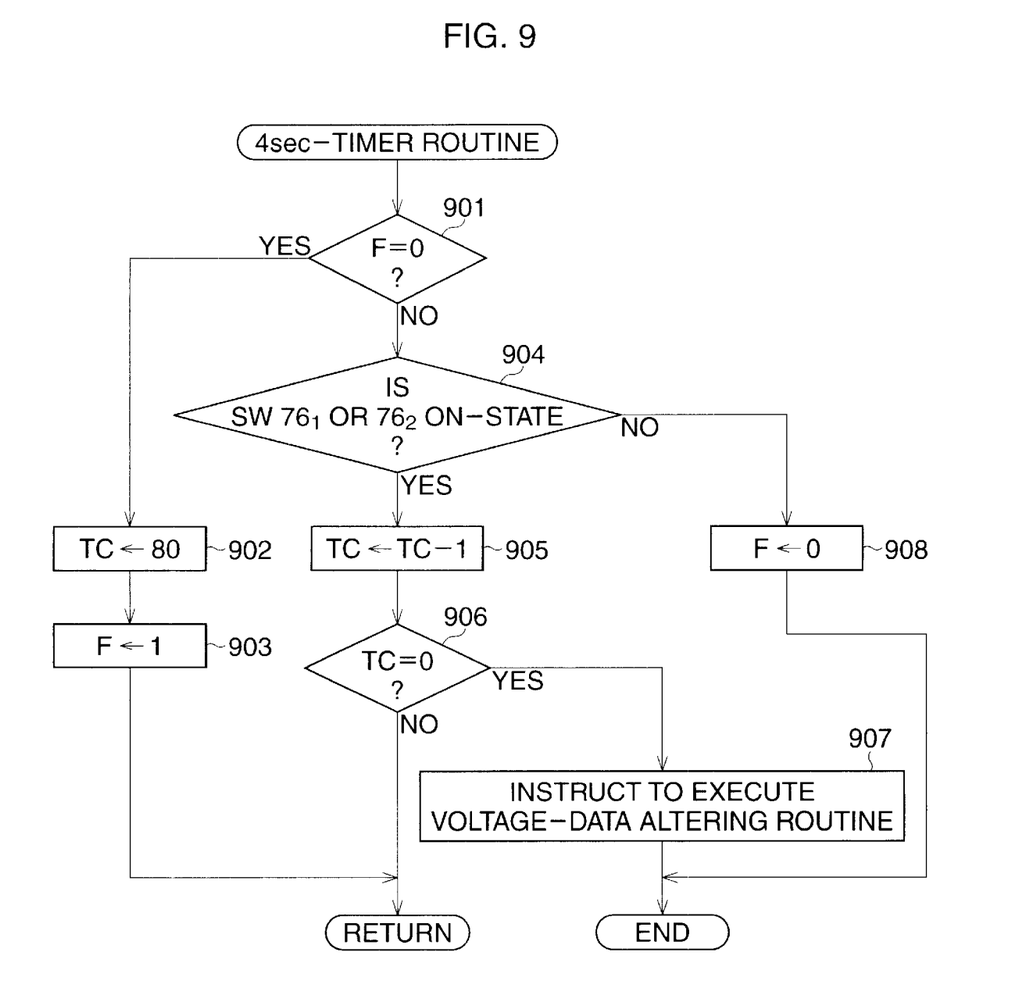
FIG. 9 is a flowchart of a 4 sec-timer routine executed in the system controller of the image-signal processing unit.

FIG. 9 shows a flowchart of a 4 sec-timer routine for monitoring whether the ON-state of each switch ($76_1$, $76_2$) is continuous over 4 sec. Note that the 4 sec-timer routine is formed as a time-interruption routine executed at predetermined regular time intervals of, for example, 50 ms, and that the execution of the 4 sec-timer routine is started when either the switch $76_1$ or $76_2$ is turned ON.

Initially, at step 901, it is determined whether a flag F is "0" or "1". If F=0, the control proceeds to step 902, in which a time counter TC is initialized to "80". Then, at step 903, the flag F is set to "1", and the routine once ends.

Note, the flag F serves as an initialization flag for the time counter TC. Namely, when F=0, the time counter TC is given the initial setting of "80" (step 902).

When the routine is again executed after 50 ms has elapsed, the control proceeds from step 901 to step 904, in which it is determined whether either the switch $76_1$ or $76_2$ is in the ON-state. If either the switch $76_1$ or $76_2$ is in the ON-state, the control proceeds to step 905, in which the value of the time counter TC is decremented by "1". Then, at step 906, it is determined whether the value of the time counter TC has reached "0". If TC≠0, the routine once ends.

Thereafter, although the routine is repeatedly executed every 50 ms, the value of the time counter TC is decremented by one every 50 ms as long as either the switch $76_1$ or $76_2$ is in the ON-state. At step 906, when it is confirmed that the value of the time counter TC has reached "0", i.e. a time of 4 sec (50 ms×80) has elapsed, the control proceeds to step 907, in which execution of a voltage-data-altering routine is instructed. Thereafter, the 4 sec-timer routine ends. Note, the voltage-data-altering routine will be explained in detail hereinafter with reference to FIG. 10.

On the other hand, when it is confirmed that either the switch $76_1$ or $76_2$ has been turned OFF (step 904) before the value of the time counter TC reaches "0", the control proceeds to step 908, in which the flag F is set to "0", and the 4 sec-timer routine ends.

Figure 10:
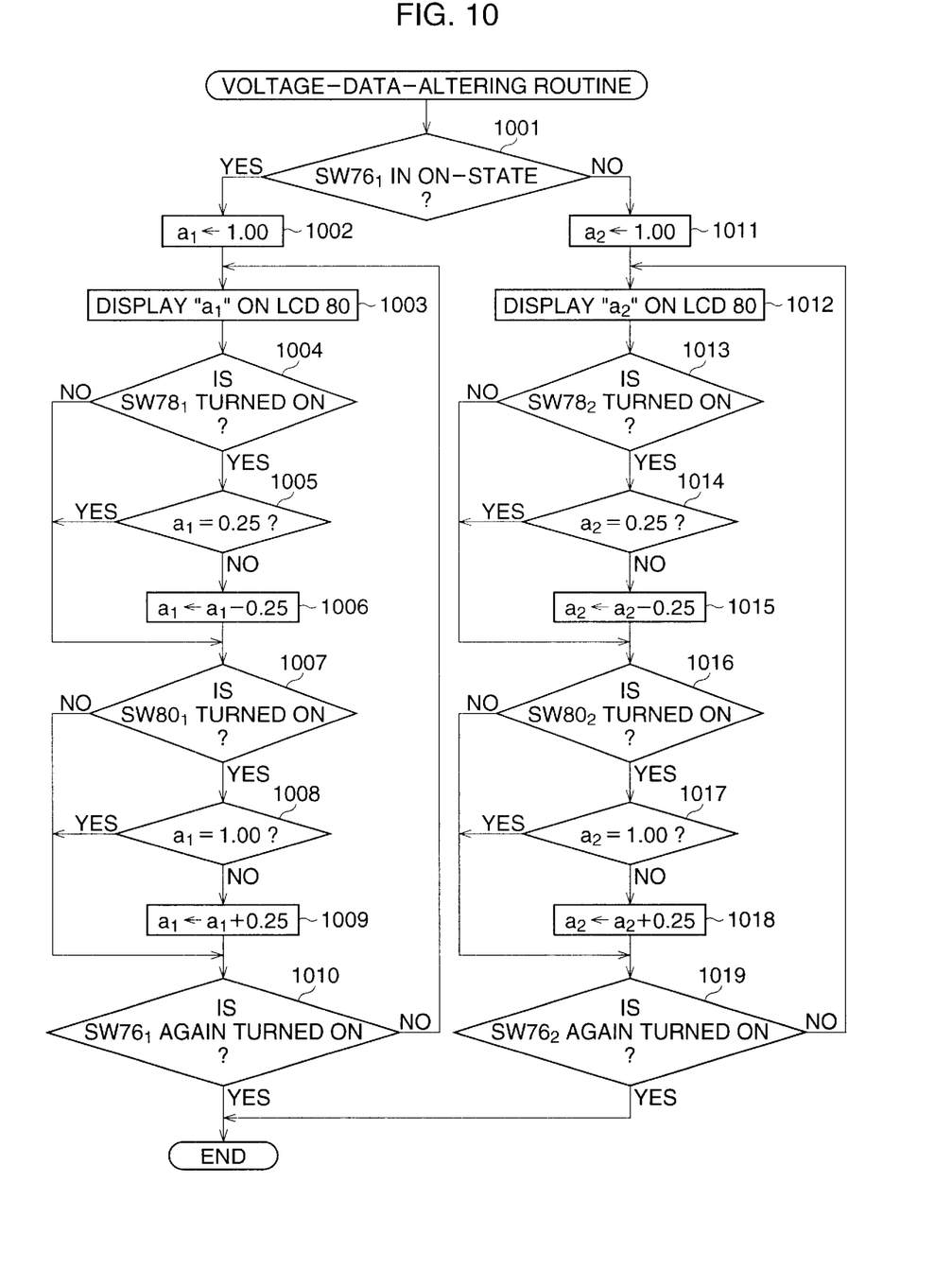
FIG. 10 is a flowchart of another voltage-data-altering routine executed in the system controller of the image-signal processing unit.

FIG. 10 shows a flowchart of the voltage-data-altering routine (step 907). Note that the voltage-data-altering routine is formed as a time-interruption routine executed at predetermined regular time intervals of, for example, 20 ms.

At step 1001, it is determined whether the switch $76_1$ has been in the ON-state for over 4 sec. If it is confirmed that the switch $76_1$ has been ON, the control proceeds to step 1002, in which a value of "1.00", representing an amplification factor, is set in a variable $a_1$. At this time, the digital voltage data, corresponding to the value (1.00) of the variable $a_1$, overwrites the first digital voltage stored in the EEPROM 54E.

At step 1003, the value of the variable $a_1$ is displayed on a liquid crystal display (LCD) 82 provided on the front panel 26 (FIG. 5). Preferably, the value of the variable $a_1$ is continuously flashed on the LCD 82 such that an operator's attention is attracted to the flashed value of the variable $a_1$.

At step 1004, it is determined whether the switch $78_1$ has been turned ON. If it is confirmed that the switch $78_1$ has been turned ON, the control proceeds to step 1005, in which it is determined whether the value of the variable $a_1$ is the minimum value or "0.25".

If $a_1 \neq 0.25$, the control proceeds to step 1006, in which the following calculation is executed:

$$a_1 \leftarrow a_1 - 0.25$$

At this time, digital voltage data, corresponding to a value of the variable $a_1$, overwrites the first digital voltage data stored in the EEPROM 54E.

At step 1004, when there is no confirmation that the switch $78_1$ has been turned ON, the control skips steps 1005 and 1006 to step 1007. Also, at step 1005, when the value of the variable $a_1$ is the minimum value (0.25), the control skips step 1006 to step 1007.

At step 1007, it is determined whether the switch $80_1$ has been turned ON. If it is confirmed that the switch $80_1$, has been turned ON, the control proceeds to step 1008, in which it is determined whether the value of the variable $a_1$ is the maximum value or "1.00".

If $a_1 \neq 1.00$, the control proceeds to step 1009, in which the following calculation is executed:

$$a_1 \leftarrow a_1 + 0.25$$

At this time, digital voltage data, corresponding to a value of the variable $a_1$, overwrites the first digital voltage data stored in the EEPROM 54E.

At step 1007, when it is not confirmed that the switch $80_1$ has been turned ON, the control skips steps 1008 and 1009 to step 1010. Also, at step 1008, when the value of the variable $a_1$ is the maximum value (1.00), the control skips step 1009 to step 1010.

At step 1010, it is determined whether the switch $76_1$ has been again turned ON. If the switch $76_1$ has not been turned ON again, the control returns to step 1003. Namely, the routine comprising steps 1003 to 1010 is executed at 20 ms intervals until it is confirmed that the switch $76_1$ has been turned ON again. At step 1010, when it is confirmed that the switch $76_1$ has been turned ON again, this routine ends, resulting in an alteration of the first voltage data stored in the EEPROM 54E.

At step 1001, when the switch $76_1$ has not been in the ON-state for over 4 sec, i.e. when the switch $76_2$ has been in the ON-state for over 4 sec, the control proceeds to step 1011, in which a value of "1.00", representing an amplification factor, is set in a variable $a_2$. At this time, the digital voltage data, corresponding to the value (1.00) of the variable $a_2$, overwrites the second digital voltage stored in the EEPROM 54E.

At step 1012, the value of the variable $a_2$ is displayed on the LCD 82 provided on the front panel 26 (FIG. 5). Preferably, the display of the value of the variable $a_2$ is continuously flashed on the LCD 82 such that the operator's attention is attracted to the flashed value of the variable $a_2$.

At step 1013, it is determined whether the switch 78$_2$ has been turned ON. If it is confirmed that the switch 78$_2$ has been turned ON, the control proceeds to step 1014, in which it is determined whether the value of the variable $a_2$ is the minimum value or "0.25".

If $a_2 \neq 0.25$, the control proceeds to step 1015, in which the following calculation is executed:

$$a_2 \leftarrow a_2 - 0.25$$

At this time, digital voltage data, corresponding to a value of the variable $a_2$, overwrites the second digital voltage data stored in the EEPROM 54E.

At step 1013, when it is not confirmed that the switch 78$_2$ has been turned ON, the control skips steps 1014 and 1015 to step 1016. Also, at step 1014, when the value of the variable $a_2$ is the minimum value (0.25), the control skips step 1015 to step 1016.

At step 1016, it is determined whether the switch 80$_2$ has been turned ON. If it is confirmed that the switch 80$_2$ has been turned ON, the control proceeds to step 1017, in which it is determined whether the value of the variable $a_2$ is the maximum value or "1.00".

If $a_2 \neq 1.00$, the control proceeds to step 1018, in which the following calculation is executed:

$$a_2 \leftarrow a_2 + 0.25$$

At this time, digital voltage data, corresponding to a value of the variable $a_2$, overwrites the second digital voltage data stored in the EEPROM 54E.

At step 1016, when it is not confirmed that the switch 80$_2$ has been turned ON, the control skips steps 1017 and 1018 to step 1019. Also, at step 1017, when the value of the variable $a_2$ is the maximum value (1.00), the control skips step 1018 to step 1019.

At step 1019, it is determined whether the switch 76$_2$ has been turned ON again. If the switch 76$_2$ has not been turned ON again, the control returns to step 1012. Namely, the routine comprising steps 1012 to 1019 is executed at 20 ms intervals until it is confirmed that the switch 76$_2$ has been turned ON again. At step 1019, when it is confirmed that the switch 76$_2$ has been turned ON again, this routine ends, resulting in an alteration of the second voltage data stored in the EEPROM 54E.

As is apparent from the foregoing, according to the present invention, since it is possible to manually and easily alter a peak-to-peak level of the compound-synchronizing-signal component of the component-type color video signal, a domestic TV monitor can be incorporated into an electronic endoscope system without any troublesome modification to either the electronic endoscope system or the domestic monitor.

Finally, it will be understood by those skilled in the art that the foregoing description is of preferred embodiments of the system, and that various changes and modifications may be made to the present invention without departing from the spirit and scope thereof.

The present disclosure relates to subject matters contained in Japanese Patent Applications No. 11-339580 (filed on Nov. 30, 1999) which is expressly incorporated herein, by reference, in its entirety.

What is claimed is:

1. An electronic endoscope system including a scope having an image sensor provided at a distal end thereof to generate image-pixel signals, and an image-signal processing unit that produces a video signal based on the image-pixel signals, which system comprises:

an alteration system that alters a peak-to-peak level of a synchronizing-signal component of said video signal; and a manual setting system that manually operates said alteration system to perform the alteration of the peak-to-peak level of said synchronizing-signal component.

2. An electronic endoscope system as set forth in claim 1, wherein said manual setting system is constituted such that the alteration of the peak-to-peak level of said synchronizing-signal component is stepwise performed by said alteration system.

3. An electronic endoscope system as set forth in claim 1, wherein said alteration system comprises a multiplier, and said manual setting system comprises a manual digital switch that produces code data, a multiplier-factor of said multiplier being altered in accordance with the code data produced by said manual digital switch.

4. An electronic endoscope system as set forth in claim 1, wherein said alteration system comprises a voltage-controlled amplifier, an amplification factor of which is altered in accordance with a level of a voltage signal applied thereto, and said manual setting system comprises a manual digital switch that produces code data, and a voltage signal generator that generates the voltage signal such that the level of said voltage signal is altered in accordance with the code data produced by said manual digital switch.

5. An electronic endoscope system as set forth in claim 1, wherein said alteration system comprises a voltage-controlled amplifier, an amplification factor of which is altered in accordance with a level of a voltage signal applied thereto, and said manual setting system comprises a storage system that stores voltage data, a voltage signal generator that generates the voltage signal such that the level of said voltage signal is altered in accordance with the voltage data stored in said storage system, and a manual-altering system that manually alters the voltage data stored in said storage system.

6. An electronic endoscope system as set forth in claim 4, wherein said storage system comprises a non-volatile memory, such as an electrically erasable programmable read-only memory.

7. An electronic endoscope system including a scope having an image sensor provided at a distal end thereof, to generate image-pixel signals, and an image-signal processing unit that produces a first video signal and a second video signal based on the image-pixel signals, which system comprises:

a first alteration system that alters a peak-to-peak level of a synchronizing-signal component of said first video signal;

a first manual setting system that manually operates said first alteration system to perform the alteration of the peak-to-peak level of the synchronizing-signal component of said first video signal;

a second alteration system that alters a peak-to-peak level of a synchronizing-signal component of said second video signal; and a second manual setting system that manually operates said second alteration system to perform the alteration of the peak-to-peak level of the synchronizing-signal component of said second video signal.

8. The electronic endoscope system according to claim 1, wherein said image sensor is a solid state image sensor.

9. The electronic endoscope system according to claim 7, wherein said image sensor is a solid state image sensor.

\* \* \* \* \*